(12) United States Patent
Mordaunt

(10) Patent No.: US 8,801,185 B2
(45) Date of Patent: Aug. 12, 2014

(54) OPHTHALMIC INSPECTION LENS

(75) Inventor: David H Mordaunt, Los Gatos, CA (US)

(73) Assignee: EOS Holdings, LLC, Los Gatos, CA (US)

( * ) Notice: Subject to any disclaimer, the term of this patent is extended or adjusted under 35 U.S.C. 154(b) by 0 days.

(21) Appl. No.: 13/429,414

(22) Filed: Mar. 25, 2012

(65) Prior Publication Data

US 2012/0242957 A1     Sep. 27, 2012

Related U.S. Application Data

(60) Provisional application No. 61/465,901, filed on Mar. 25, 2011.

(51) Int. Cl.
*A61B 3/117* (2006.01)
*A61B 3/125* (2006.01)

(52) U.S. Cl.
CPC ............... *A61B 3/125* (2013.01); *A61B 3/117* (2013.01)
USPC .......................................................... 351/219

(58) Field of Classification Search
USPC ......... 359/802–803, 641–643, 647, 808–812, 359/818, 830; 351/200, 205, 207, 219
See application file for complete search history.

(56) References Cited

U.S. PATENT DOCUMENTS

| | | | | |
|---|---|---|---|---|
| 5,841,510 | A * | 11/1998 | Roggy | 351/218 |
| 2008/0131113 | A1* | 6/2008 | Chang | 396/529 |
| 2009/0185135 | A1* | 7/2009 | Volk | 351/219 |
| 2010/0091244 | A1 | 4/2010 | Volk | |
| 2012/0113392 | A1* | 5/2012 | Heacock | 351/219 |

* cited by examiner

*Primary Examiner* — Ricky Mack
*Assistant Examiner* — Robert E Tallman
(74) *Attorney, Agent, or Firm* — Innovation Counsel LLP

(57) ABSTRACT

Single piece ophthalmic inspection devices are provided having a continuous 3-dimensional molded surface preferably made out of plastic. The devices are relatively easier and cheaper to manufacture than existing inspection lenses. The smooth continuous edges are advantages to prevent damage to tissue as well to stop foreign objects accumulating in e.g. the clear regions of the lens. Ergonomic features are built into the ophthalmic inspection device provide for superior control of the device on the patient's eye. In addition, textured knurled or grooved surface provide desired finger grip and control of the device.

7 Claims, 2 Drawing Sheets

OPHTHALMIC INSPECTION LENS

CROSS-REFERENCE TO RELATED APPLICATIONS

This application claims priority from U.S. Provisional Patent Application 61/465,901 filed Mar. 25, 2011, which is incorporated herein by reference.

FIELD OF THE INVENTION

The invention relates to ophthalmic inspection lenses.

BACKGROUND OF THE INVENTION

Ophthalmic inspection lenses are utilized by physicians in conjunction with a slit lamp, ophthaloscope or operating microscope to view inside the eye to inspect, diagnose and treat various eye conditions, such as macular edema and glaucoma.

There is a range of ophthalmic inspection lenses utilized for viewing specific regions of the eye. General inspection lenses have a single optical element and a range of optical prescription from 15 to 90D and are freely held in front of cornea without making contact. For precise inspection and treatment of specific anatomical regions of the eye specialty lenses are utilized with multiple optical elements, which are designed to be utilized with an optical surface in contact with the anterior surface of the cornea, such as, capsulotomy, gonio, and retina lenses.

The current art for ophthalmic inspection lens has at least one optical lens and a metal housing, whereby these multiple components are glued or mechanically retained together as single assembly. These lenses have a high cost as they require precision optics, precision mating of parts and a high quality of workmanship in the complete assembly.

SUMMARY OF THE INVENTION

The present invention provides ophthalmic inspection devices. In one embodiment, the ophthalmic inspection device has a circular lens with a central optically clear region which distinguishes a concave tissue interface surface and a convex inspection surface. A tubular cylindrical lens handle is concentric with the circular lens and protrudes laterally from the convex inspection surface. An inspection device base is ring-shaped and concentric with the circular lens. The inspection device base abuts a rim of the concave tissue interface surface. A finger rest feature is disposed between the tubular cylindrical lens handle and the inspection device base. The circular lens, tubular cylindrical lens handle, finger rest feature and inspection device base are a single piece, which is a continuous 3-dimensional molded surface. In a preferred embodiment, the single piece is a single plastic piece.

In one aspect of the first embodiment, the surface of the tubular cylindrical lens handle prevents light reflection through the tubular cylindrical lens handle towards the circular lens or in another aspect the surface of the tubular cylindrical lens handle has an anti-reflection coating.

In still another aspect of the first embodiment, the surface of the inspection device base prevents light reflection through the inspection device base towards the circular lens or in still another aspect the surface of the inspection base has an anti-reflection coating.

In still another aspect of the first embodiment, the surface of the finger rest feature prevents light reflection through the finger rest feature towards the circular lens or in still another aspect the surface of the finger rest feature has an anti-reflection coating.

In still another aspect of the first embodiment, the finger rest feature has an ergonomic feature for indication of the orientation of the ophthalmic inspection device.

In yet another aspect of the first embodiment, the outerside of the tubular cylindrical lens handle has an ergonomic feature for indication of the orientation of the ophthalmic inspection device.

In a second embodiment, the ophthalmic inspection device has a circular lens with a central optically clear region which distinguishes a convex tissue interface surface and a convex inspection surface. The central optically clear region has an optical axis through the middle of the central optically clear region. A tubular cylindrical lens handle is concentric with the circular lens and protrudes laterally from the convex inspection surface and from the convex tissue interface surface. The size of the lens handle at the convex inspection surface is the same or different from the size of the lens handle at the convex tissue interface surface. A finger rest feature is disposed as an indentation or protrusion substantially parallel with the optical axis in the outerside of the tubular cylindrical lens handle. The circular lens, tubular cylindrical lens handle, and finger rest feature are a single piece. In one aspect the single piece is a continuous 3-dimensional molded surface, and in another aspect the single piece is a continuous 3-dimensional molded surface except for the finger rest feature. In a preferred embodiment, the single piece is a single plastic piece.

In still another aspect of the second embodiment, the surface of the tubular cylindrical lens handle prevents light reflection through the tubular cylindrical lens handle towards the circular lens or in still another aspect the surface of the tubular cylindrical lens handle has an anti-reflection coating.

In still another aspect of the second embodiment, surface of the finger rest feature prevents light reflection through the finger rest feature towards the circular lens or in still another aspect the surface of the finger rest feature has an anti-reflection coating.

In still another aspect of the second embodiment, the finger rest feature has an ergonomic feature for indication of the orientation of the ophthalmic inspection device.

In yet another aspect of the second embodiment, the outerside of the tubular cylindrical lens handle has an ergonomic feature for indication of the orientation of the ophthalmic inspection device.

The embodiments of the ophthalmic inspection device have several advantages. For example, the ophthalmic inspection device is a single piece injection molded device, which is relatively cheaper and easier to produce than current manufacturing processes for existing lenses. The smooth edges are important to prevent damage to tissue as well to stop foreign objects accumulating in e.g. the clear regions of the lens. Ergonomic features are built into the ophthalmic inspection device provide for superior control of the device on the patient's eye. In addition, textured knurled or grooved surface provide desired finger grip and control of the device.

BRIEF DESCRIPTION OF THE DRAWINGS

FIG. 1a shows a cut away view, FIG. 1b shows an oblique top view, and FIG. 1c shows an oblique bottom view.

2a shows a cut away view, FIG. 2b shows an oblique top view, and FIG. 2c shows an oblique bottom view.

DETAILED DESCRIPTION

Figure 1:
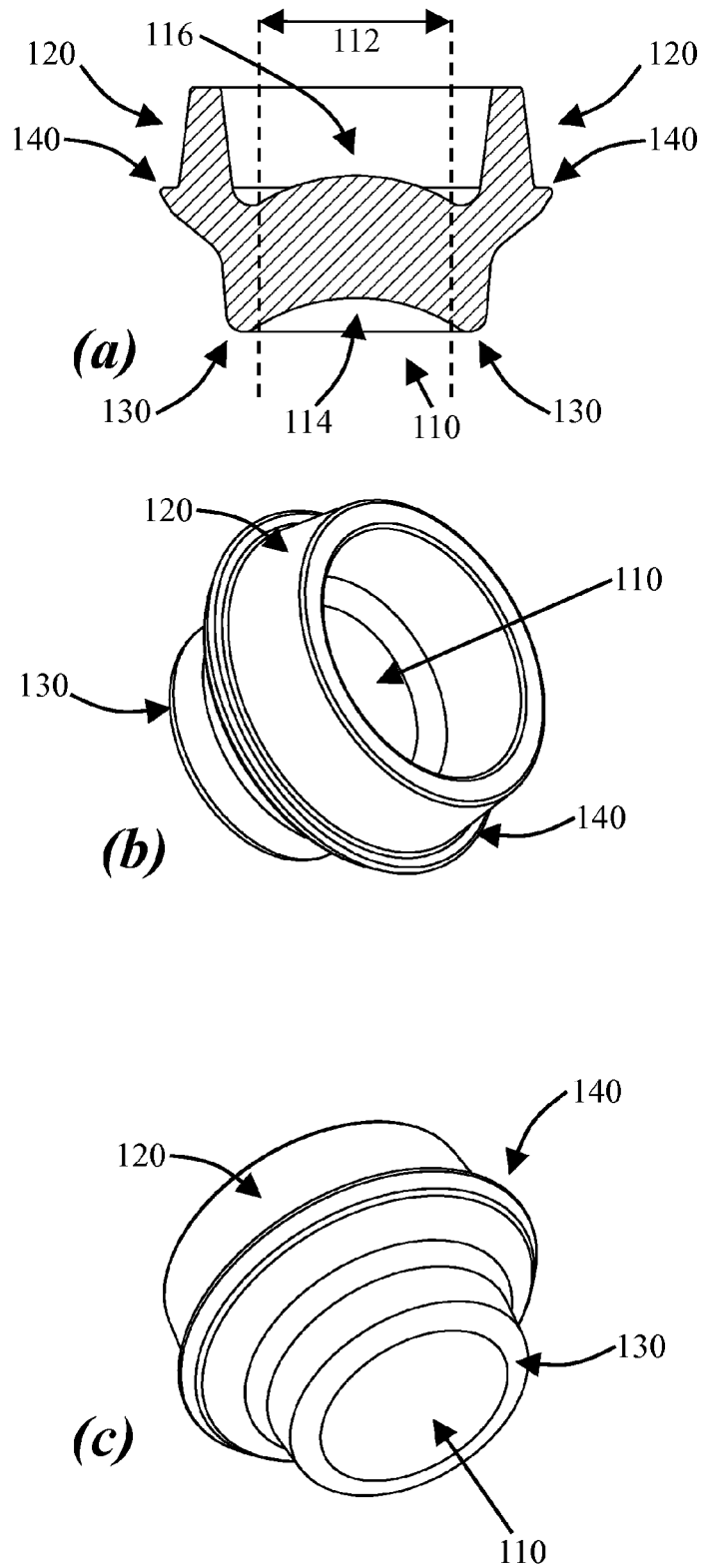
FIGS. 1a-c show an ophthalmic inspection device according to a first exemplary embodiment of the invention.

Embodiments are provided to indirect and direct ophthalmoscopic lenses as used by ophthalmologists and optometrists for diagnosis and treatment of ocular tissue. FIGS. 1a-c show an ophthalmic inspection device with a circular lens 110. The lens 110 has a central optically clear region 112 with a concave tissue interface surface 114 and a convex inspection surface 116. The ophthalmic inspection device further has a tubular cylindrical lens handle 120, which is concentric with the circular lens 110 and protrudes laterally from the convex inspection surface 116. The ophthalmic inspection device further has an inspection device base 130, which is ring-shaped and concentric with the circular lens 110. The inspection device base 130 abuts a rim of the concave tissue interface surface 114. The ophthalmic inspection device further has a finger rest feature 140, which is disposed between the tubular cylindrical lens handle 120 and the inspection device base 130.

The circular lens 110, the tubular cylindrical lens handle 120, the finger rest feature 140 and the inspection device base 130 are a single piece, which is a continuous (smooth) 3-dimensional molded surface. In a preferred embodiment, the single piece ophthalmic inspection device is made out of plastic.

In one embodiment, the surface of the tubular cylindrical lens handle prevents light reflection through the tubular cylindrical lens handle towards the circular lens. In another embodiment, the surface of the tubular cylindrical lens handle has an anti-reflection coating. Similarly, the surface of the inspection device base prevents light reflection through the inspection device base towards the circular lens or the surface of the inspection base has an anti-reflection coating. Similarly, the surface of the finger rest feature prevents light reflection through the finger rest feature towards the circular lens or said surface of the finger rest feature has an anti-reflection coating. In one embodiment, the anti-reflection features (whether it is frosting, grooves, knurles, coating, or the like) are created as part of the single piece molding process of the ophthalmic inspection device. In another embodiment, these features are created after the single piece molding process of the ophthalmic inspection device.

In one embodiment, the finger rest feature has an ergonomic feature for tactile indication of the orientation of the ophthalmic inspection device to a user. In another embodiment, the outerside of the tubular cylindrical lens handle has an ergonomic feature for tactile indication of the orientation of the ophthalmic inspection device to a user.

The embodiment in FIG. 1 can be molded with 2-piece mold. One-piece molding the top section of the lens and other-piece molding the lower section lens with parting line at the finger rest feature, more specifically at its widest diameter. High quality optical surfaces are achieved with the appropriate care to mold quality polished surface finish, fill rate, pressure and molding time. Frosted textured surfaces could be achieved with the corresponding textured finish on regions of the mold. On the tubular cylindrical lens handle there could be an appropriate draft of a few degrees maintained orthogonal to the mold parting line. The linear knurled features could be achieved with 3D grooved lines on this drafted region, these 3D grooves are in a regular repeating pattern around the cylindrical lens handle, and could also be orthogonal to the parting line of the mold allowing efficient demolding, i.e., removal of the part from the mold.

Referring again to FIGS. 1(a)-1(c), the outer surfaces of ophthalmic lens 110 in a region from the finger rest shelf 140 to the ring-shaped base 130 may have a frosted texture directly from the mold to prevent reflection into the central optically clear region 112 from these surfaces for internal light, and to prevent coherent images from external light sources.

FIGS. 2a-c show an ophthalmic inspection device with a circular lens 210. The lens 210 has a central optically clear region 212 with a convex tissue interface surface 214 and a convex inspection surface 216. The central optically clear region has an optical axis 218 through the middle of the central optically clear region 212. The ophthalmic inspection device further has a tubular cylindrical lens handle 220, which is concentric with the circular lens 210 and protrudes laterally from the convex inspection surface 216 and from the convex tissue interface surface 214. The size of the lens handle at the convex inspection surface (indicated by 222) could be the same or could be different from the size of the lens handle at the convex tissue interface surface (indicated by 224). The ophthalmic inspection device further has a finger rest feature 230, which is disposed as an indentation (shown) or protrusion (not shown) substantially parallel with the optical axis 218 in the outerside of the tubular cylindrical lens handle 220.

The circular lens 210, the tubular cylindrical lens handle 220, and the finger rest feature 230 are a single piece, which is a continuous (smooth) 3-dimensional molded surface (i.e. the edges of the finger rest feature are all smooth and continuous, not shown). In other embodiment, the circular lens 210, the tubular cylindrical lens handle 220, and the finger rest feature 230 are a single piece, which is a continuous (smooth) 3-dimensional molded surface except for the edges of the finger rest feature 230. In a preferred embodiment, the single piece ophthalmic inspection device is made out of plastic.

In one embodiment, the surface of the tubular cylindrical lens handle prevents light reflection through the tubular cylindrical lens handle towards the circular lens. In another embodiment, the surface of the tubular cylindrical lens handle has an anti-reflection coating. Similarly, the surface of the finger rest feature prevents light reflection through the finger rest feature towards the circular lens or said surface of the finger rest feature has an anti-reflection coating. In one embodiment, the anti-reflection features (whether it is frosting, grooves, knurles, coating, or the like) are created as part of the single piece molding process of the ophthalmic inspection device. In another embodiment, these features are created after the single piece molding process of the ophthalmic inspection device.

In one embodiment, the finger rest feature has an ergonomic feature for tactile indication of the orientation of the ophthalmic inspection device to a user. In another embodiment, the outerside of the tubular cylindrical lens handle has an ergonomic feature for tactile indication of the orientation of the ophthalmic inspection device to a user.

Figure 2:
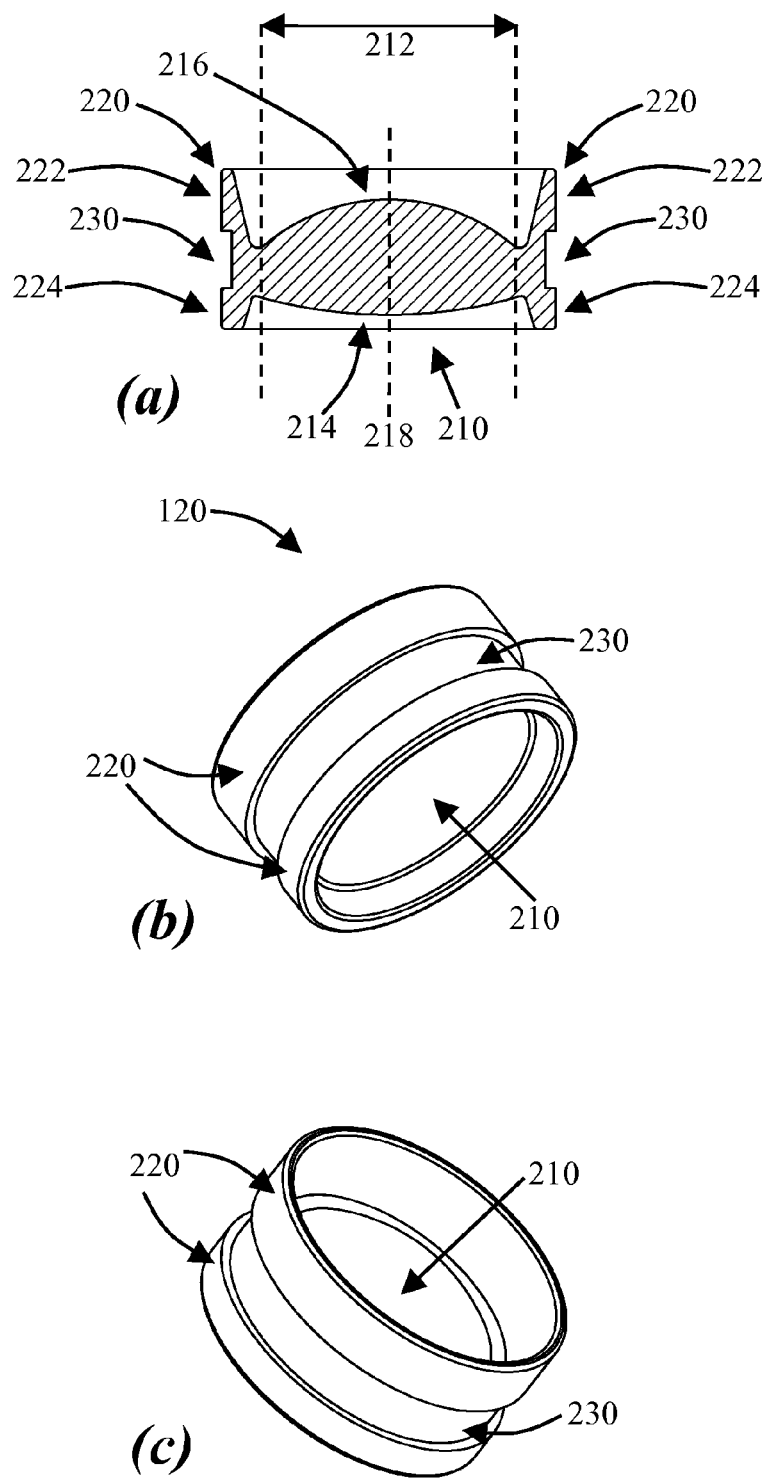
FIGS. 2a-c show an ophthalmic inspection device according to a second exemplary embodiment of the invention. FIG.

The embodiment in FIG. 2 can be molded with 2-piece mold with 3 (or more) additional side action pieces. One-piece molding the top section of the lens and other-piece molding the lower section lens with parting line at the finger rest feature. In this embodiment there is minimal or no draft on the cylindrical lens handle, and there is an indentation for the finger rest feature, therefore side action pieces are required in the mold. As we want to create a knurled pattern around the circumference of the cylindrical lens handle, 3 (or more side) action piece are required in the mold to apply the appropriate degree of shape to the 3D features in the knurl pattern during molding. Once the molded lens has formed, the side action pieces move outward in a radial fashion, so as not to interfere with the molded part and its knurled features. The region of the finger rest also could incorporate an impression of text, allowing product and company branding on this lens product.

Variations

The ophthalmic inspection devices can be varied such that the radius in tissue contact (e.g. the cornea) has a radius in the range of 7.5-10 mm, more nominally 8.5 mm, or slightly larger than the nominal the nominal radius of curvature so the cornea is not distorted. The outerside of the ophthalmic inspection device can be used to indicate lens or brand information and could also come directly from the single injection mold process. Another variation could pertain to the addition of a suction to the cornea outside the region of the central optically clear region. For example, channels could go through the tubular cylindrical lens handle (not shown) and used as vacuum suction channels. In another variation one could use for example 1 or 2 (non)-diffractive optical elements and/or protective windows mounted in a housing in between the tubular cylindrical lens handle above the inspection surface (not shown). The diffractive optical elements should be designed such that they minimize achromatic aberrations and (optionally) have antireflective coatings in the visible region of the spectrum.

What is claimed is:

1. An ophthalmic inspection lens comprising:
   a circular central optically clear region having a concave tissue interface surface and a convex inspection surface;
   a tubular cylindrical handle concentric with the optically clear region, protruding laterally from the convex inspection surface, and extending parallel to an optical axis of the lens beyond the convex inspection surface;
   a ring-shaped base concentric with the optically clear region and abutting a rim of the concave tissue interface surface; and
   a finger rest shelf disposed between and protruding laterally from the tubular cylindrical handle and the ring-shaped base;
   wherein the lens is a single piece of injection molded plastic, and outer surfaces of the lens in a region from the finger rest shelf to the ring-shaped base are molded with a frosted texture preventing internal reflection of light from those surfaces into the central optically clear region.

2. The ophthalmic inspection lens of claim 1, wherein the frosted texture prevents transmission of images from external light sources through those surfaces into the optically clear region.

3. The ophthalmic inspection lens of claim 1, wherein outer surfaces of the tubular cylindrical handle are molded with a texture improving finger grip.

4. The ophthalmic inspection lens of claim 3, wherein the molded texture of the outer surfaces of the tubular cylindrical handle comprises a repeating pattern of molded grooves running orthogonally to a mold parting line on the inspection lens.

5. The ophthalmic inspection lens of claim 1, comprising a mold parting line located at a widest diameter of the finger rest shelf.

6. The ophthalmic inspection lens of claim 1, wherein the finger rest shelf comprises an indication of the orientation of the ophthalmic inspection lens.

7. The ophthalmic inspection lens of claim 1, wherein the outer side of the tubular cylindrical lens handle comprises an indication of the orientation of the ophthalmic inspection lens.

* * * * *